(12) United States Patent
Tappehorn et al.

(10) Patent No.: US 11,452,837 B2
(45) Date of Patent: Sep. 27, 2022

(54) VALVE MODULE FOR A VENTILATION SYSTEM, VENTILATION TUBE DEVICE, VENTILATOR, VENTILATION SYSTEM AS WELL AS PROCESS FOR SEVERING AND ESTABLISHING A FLUID-COMMUNICATING CONNECTION

(71) Applicant: Drägerwerk AG & Co. KGaA, Lübeck (DE)

(72) Inventors: Ludger Tappehorn, Lübeck (DE); Erwin Broos, Ratekau (DE); Birger Landwehr, Lübeck (DE)

(73) Assignee: DRÄGERWERK AG & CO. KGAA, Lübeck (DE)

(*) Notice: Subject to any disclaimer, the term of this patent is extended or adjusted under 35 U.S.C. 154(b) by 511 days.

(21) Appl. No.: 16/667,299

(22) Filed: Oct. 29, 2019

(65) Prior Publication Data
US 2020/0129726 A1    Apr. 30, 2020

(30) Foreign Application Priority Data

Oct. 30, 2018  (DE) .......................... 102018008495.8

(51) Int. Cl.
*A61M 16/20* (2006.01)
*A61M 16/00* (2006.01)
*A61M 16/08* (2006.01)

(52) U.S. Cl.
CPC ...... *A61M 16/205* (2014.02); *A61M 16/0003* (2014.02); *A61M 16/024* (2017.08);
(Continued)

(58) Field of Classification Search
CPC .............. A61M 16/024; A61M 16/203; A61M 16/205; A61M 16/0816; A61M 16/0833;
(Continued)

(56) References Cited

U.S. PATENT DOCUMENTS 4,454,893 A * 6/1984 Orchard .............. A61M 16/206
                                                128/205.24
6,158,430 A * 12/2000 Pfeiffer .................. A61M 16/00
                                                128/204.21
(Continued)

FOREIGN PATENT DOCUMENTS

EP         0938909 A1    9/1999

*Primary Examiner* — Joseph D. Boecker
*Assistant Examiner* — Thomas W Greig
(74) *Attorney, Agent, or Firm* — McGlew and Tuttle, P.C.

(57) ABSTRACT

A valve module (20) for a ventilation system (100), includes a tube interface (21) for connection to a counter-tube interface (14) of an exhalation end (13) of a ventilation tube element (11) as well as a device interface (22) for connection to a counter-device interface (114) of an exhalation port (113) of a ventilator (110). The device interface has an exhalation valve section (24) providing an exhalation flow (93) of exhaled air (92) with an exhalation pressure (94). The exhaled air from the tube interface (21) flows through a module space (23). A ventilation tube device (10), the ventilator (110) as well as the ventilation system are provided with the valve module. Processes are provided for severing and establishing a connection between the device interface, the ventilation tube device and the counter-device interface of the exhalation port of the ventilator of the ventilation system.

23 Claims, 5 Drawing Sheets

(52) U.S. Cl.
CPC . *A61M 16/0833* (2014.02); *A61M 2016/0027* (2013.01); *A61M 2205/505* (2013.01)

(58) Field of Classification Search
CPC ............ A61M 16/206; A61M 16/0057; A61M 16/0066; A61M 16/01; A61M 16/0883
See application file for complete search history.

(56) References Cited

U.S. PATENT DOCUMENTS

| | | |
|---|---|---|
| 8,656,031 B2 | 2/2014 | Iwase |
| 2010/0269829 A1 | 10/2010 | Hansmann et al. |
| 2011/0284007 A1 | 11/2011 | Pierre |
| 2012/0085348 A1* | 4/2012 | Chalvignac ........... A61M 16/20 |
| | | 128/205.24 |
| 2016/0058967 A1* | 3/2016 | McCormick ...... A61M 16/0883 |
| | | 128/205.24 |

\* cited by examiner

VALVE MODULE FOR A VENTILATION SYSTEM, VENTILATION TUBE DEVICE, VENTILATOR, VENTILATION SYSTEM AS WELL AS PROCESS FOR SEVERING AND ESTABLISHING A FLUID-COMMUNICATING CONNECTION

CROSS REFERENCE TO RELATED APPLICATIONS

This application claims the benefit of priority under 35 U.S.C. § 119 of German Application 10 2018 008 495.8, filed Oct. 30, 2018, the entire contents of which are incorporated herein by reference.

TECHNICAL FIELD

The present invention pertains to a valve module for a ventilation system (also known as a respiration system) for ventilating a patient, having a tube interface for fluid-tight connection to a counter-tube interface of an exhalation end of a ventilation tube element as well as a first device interface for fluid-tight connection to a first counter-device interface of an exhalation port of a ventilator (also known as a respirator) of the ventilation system, wherein the tube interface and the first device interface are connected in a fluid-communicating manner at least by a module space, and wherein the first device interface has an exhalation valve section for providing an exhalation flow of exhaled air with an exhalation pressure from the valve module at least from time to time, the exhaled air arriving from the tube interface and flowing through the module space. The present invention further pertains to a ventilation tube device for ventilating a patient by a ventilation system, having an especially at least essentially Y-shaped, continuously hollow ventilation tube element with a patient end for providing breathing air to the patient and for removing exhaled air of the patient, with an inhalation end and with an exhalation end, wherein the inhalation end has, for providing breathing air, a second device interface for fluid-tight connection to a second counter-device interface of an inhalation port of a ventilator of the ventilation system, and the exhalation end has a counter-tube interface. Another aspect of the present invention pertains to a ventilator for ventilating a patient, having an inhalation port for providing breathing air for the patient, and an exhalation port for removing exhaled air from the patient.

The present invention pertains, moreover, to a process for severing a fluid-communicating connection between a first device interface of a ventilation tube device and a first counter-device interface of an exhalation port of a ventilator of a ventilation system. Corresponding to another aspect, the present invention pertains to a process for establishing a fluid-communicating connection between a first device interface of a ventilation tube device at a first counter-device interface of an exhalation port of a ventilator of a ventilation system.

TECHNICAL BACKGROUND

It is known, in principle, in the medical care of patients that a patient may be ventilated, if necessary, mechanically by means of a ventilator. This ventilation process is usually determined by a plurality of ventilation parameters, which can be set especially by the operating staff of the ventilator, for example, physicians and/or the nursing staff. It may be necessary for a transfer of the patient within the hospital or even for a transportation of the patient between different hospitals to transfer the ventilation process from one ventilator of a ventilation system to another ventilator of the ventilation system. Transfer units, as they are known, for example, from US 2016 058 967 A1 or EP 0 938 909 A1, may be provided for this purpose.

It proved to be especially problematic in case of such a transfer that the ventilation process is often interrupted during the transfer to the extent that a set positive end-expiratory pressure, which can represent an essential ventilation parameter, is especially frequently lost. To counteract this circumstance, it is known that valve systems can be used, which maintain this minimum exhalation pressure. However, such prior-art valve systems or valve modules have various drawbacks. Thus, such a valve module is known from US 2011 284 007 A, but it must be arranged at an end of the entire ventilation chain close to the patient, especially within the trachea of a patient. Other prior-art valve modules, disclosed, for example, in U.S. Pat. No. 8,656,031 or US 2010 269 829 A, are intended for fixed internal installation in ventilators. Thus, a subsequent arrangement of the corresponding valve modules is not possible in any of the prior-art systems.

SUMMARY

Based on this state of the art, a basic object of the present invention is to improve valve modules for ventilation systems, ventilation tube devices, ventilators, as well as ventilation systems and processes for severing and establishing fluid-communicating connections. An object of the present invention is, in particular, to provide a valve module for a ventilation system for ventilating a patient, a ventilation tube device, a ventilator as well as a ventilator system for ventilating a patient, and a process for severing and establishing a fluid-communicating connection between a first device interface of a ventilation tube device and a first counter-device interface of an exhalation port of a ventilator of a ventilation system, which make it possible in an especially simple and cost-effective manner to expand a ventilation system by a functionality of maintaining a minimum pressure during an exhalation process of the patient, wherein it is possible, in particular, to continue to use already existing interfaces between the individual elements of the ventilation system.

The above object is accomplished by a valve module for a ventilation system for ventilating a patient with features as described herein, by a ventilation tube device for ventilating a patient by a ventilation system with features as described herein, by a ventilator for ventilating a patient with features as described herein, by a ventilation system for ventilating a patient with features as described herein, by a process for severing a fluid-communicating connection between a first device interface of a ventilation tube device and a first counter-device interface of an exhalation port of a ventilator of a ventilation system with features as described herein, as well as by a process for establishing a fluid-communicating connection between a first device interface of a ventilation tube device and a first counter-device interface of an exhalation port of a ventilator of a ventilation system with features as described herein. Features and details that are described in connection with the valve module according to the present invention apply, of course, in connection with the ventilation tube device according to the present invention, with the ventilator according to the present invention, with the ventilation system according to the present invention as well as with the process according to the present invention for severing and establishing a fluid-communicating connection and vice versa, so that reference is and can always mutually be made to the individual aspects of the present invention concerning the disclosure.

According to a first aspect of the present invention, the object is accomplished by a valve module for a ventilation system for ventilating a patient, having a tube interface for fluid-tight connection to a counter-tube interface of an exhalation end of a ventilation tube element as well as a first device interface for fluid-tight connection to a first counter-device interface of an exhalation port of a ventilator of the ventilation system, wherein the tube interface and the first device interface are connected at least by a module space in a fluid-communicating manner, and wherein the first device interface has an exhalation valve section for at least partially providing an exhalation flow of exhaled air with an exhalation pressure from the valve module, the exhaled air arriving from the tube interface and flowing through the module space. A valve module according to the present invention is characterized in that the exhalation valve section has a pressure-limiting element, comprising a control section and a control element, wherein a control fluid with a control pressure can be admitted to the control element, wherein the exhalation pressure of the exhaled air can be admitted to the control section, which is functionally connected to the control element, and wherein the pressure-limiting element can be set, depending on the control pressure of the control fluid in the control element and on the exhalation pressure of the exhaled air, at least into a flow position, in which the pressure-limiting element releases the exhalation flow through the exhalation valve section, and into a blocking position, in which the pressure-limiting element blocks the exhalation flow through the exhalation valve section.

Exhalation means breathing out in the sense of the present application, i.e., a gas flow away from the patient. Inhalation correspondingly means breathing in in the sense of the present application, i.e., a gas flow towards the patient. A tube interface is especially a tube port element at the valve module. A counter-tube interface is preferably a device-side exhalation tube port at the ventilation tube device, i.e., at a tube system. Exhalation end means especially a device-side inhalation tube port. The first device interface represents especially a first device interface at the ventilation tube device, i.e., the tube system. The first counter-device interface represents especially a first coupling interface at the ventilator. The second device interface represents especially a second device interface at the ventilation tube device, i.e., the tube system. The second counter-device interface represents especially a second coupling interface at the ventilator. The blocking position is a position blocking the flow. The flow position is a position releasing the exhalation opening. The pressure-limiting element, for example, a valve for controlling the exhalation opening, is opened in the flow position.

A valve module according to the present invention for a ventilation system is intended for being arranged between a ventilation tube element and a ventilator of the ventilation system. In other words, a subsequent installation of a valve module according to the present invention, especially also during an ongoing ventilation process of a patient, can be made possible in a simple manner by, for example, the ventilation tube element being completely blocked close to the patient, and the valve module according to the present invention can then be arranged between the ventilation tube element and the ventilator. The valve module according to the present invention has especially the corresponding interfaces for this arrangement; a tube interface for arrangement at the counter-tube interface of the ventilation tube element as well as a device interface for arrangement at a counter-device interface of the ventilator. A fluid-tight arrangement of the valve module between an exhalation end of the ventilation tube element and an exhalation port of the ventilator can be made possible in this manner in an especially simple and reliable manner. To ensure the flow of the exhaled air through a valve module according to the present invention, a module space, which has especially a continuously hollow configuration, is formed between the tube interface and the first device interface. Continuously hollow means in the sense of the present invention especially that exhaled air arriving with an exhalation pressure from the patient can flow through the tube interface into the module space, it can flow through the module space in an exhalation flow in the direction of the device interface and it can again leave the valve module there, regulated and/or controlled by the pressure-limiting element. The pressure-limiting element is closed in the blocking position.

Provisions are made according to the present invention in a valve module for the exhalation valve section, which forms a part of the first device interface, to have a pressure-limiting element, comprising a control section and a control element. It can be made possible by this pressure-limiting element, in particular, that the exhalation pressure of the exhaled air of the patient will not drop below a certain minimum pressure. This can be made possible especially by the interaction according to the present invention between the control section and the control element. Thus, a control fluid, having a control pressure, can be admitted to the control element. In other words, the control element can thus be set differently, for example, by air as the control fluid, corresponding to the particular control pressure. The control section is, in turn, connected functionally to the control element and the exhalation pressure of the exhaled air can be admitted to it. In other words, the control section can thus preferably be influenced both by the exhaled air, especially by the exhalation pressure of the exhaled air, and, furthermore, also by the control fluid, which sets the control element differently based on the control pressure, and then acts on this via the functional connection to the control section. Depending on the control pressure of the control fluid in the control element, the exhalation pressure of the exhaled air, both of which act on the control section, the entire pressure-limiting element will now have at least two different positions: a flow position and a blocking position. The exhalation flow through the exhalation valve section is released in the flow position, but it is blocked in the blocking position. In other words, controlled by the control pressure of the control fluid in the control element, the pressure-limiting element can thus release or block this exhalation flow of the exhaled air depending on an exhalation pressure of the exhaled air of the patient. This may preferably be brought about, for example, in such a manner that an exhalation pressure will not drop below a set value. In other words, a minimum pressure level of exhaled air of the patient and hence a defined positive end-expiratory pressure can be ensured by the valve module according to the present invention in an especially simple and reliable manner.

Further, provisions may be made in a valve module according to the present invention for the position of the pressure-limiting element to depend on the exhalation pressure of the exhaled air and on the control pressure of the control fluid such that by selecting the control pressure, an expiratory limit pressure can be set for the exhaled air, wherein the pressure-limiting element is in its blocking position if an exhalation pressure is lower than the expiratory limit pressure and the pressure-limiting element is in its flow position if the exhalation pressure is higher than the expiratory limit pressure. Provisions may especially be made in an especially preferred manner for the expiratory limit pressure to correspond to the positive end-expiratory pressure to be set for the ventilation process of the patient. Provisions are made, as an essential feature of the present invention, for precisely this expiratory limit pressure to be able to be set by selecting the control pressure of the control fluid. In other words, a corresponding expiratory limit pressure and hence a positive end-expiratory pressure can be set for the patient by a valve module according to the present invention in a patient-dependent or patient-adapted manner. The control pressure of the control fluid is selected and set for this such that exhalation is precisely prevented in case of an exhalation pressure lower than the expiratory limit pressure by the pressure-limiting element in its blocking position. It can be ensured in this manner that the positive end-expiratory pressure can be maintained for the patient at any time.

A valve module according to the present invention may also be configured such that the control element has a control chamber with a control opening and the control section has a control diaphragm, which is flexible in at least some sections, and a control diaphragm stop, the control diaphragm stop having a flow opening for the exhalation flow of the exhaled air, wherein the control diaphragm further closes the control opening of the control chamber in a fluid-tight manner and, further, it blocks the flow opening in a fluid-tight manner in the blocking position of the pressure-limiting element and it releases the flow opening for the exhalation flow of the exhaled air in the flow position of the pressure-limiting element. In this preferred embodiment of a valve module according to the present invention, the control section and the control element have an especially compact and partially one-part or one-piece configuration. Thus, the control element has a control chamber with a control opening, which is closed by a control diaphragm, which is flexible in at least some sections. In other words, the control chamber and the control diaphragm are configured for receiving the control fluid such that the control fluid cannot escape. This has the advantage that when the control fluid is admitted to the control element, to the extent to which the control diaphragm, which has an at least partially flexible configuration, yields to this pressure and arches especially against the control diaphragm stop as part of the control section. Since the exhaled air with its exhalation pressure likewise acts on the control diaphragm as a part of the control section, the limit pressure at which the control diaphragm comes into contact with the control diaphragm stop and especially blocks same in a fluid-tight manner can thus be set directly. If the exhalation pressure of the exhaled air exceeds the limit pressure set by the control pressure, the control diaphragm is lifted off from the control diaphragm stop and the flow opening is released hereby for the exhalation flow of the exhaled air. An especially mechanically simple setting or provision of a minimum pressure of the exhaled air can be made reliably possible in this manner. A control diaphragm may be a valve diaphragm and a control diaphragm stop may be a valve seat.

A valve module according to the present invention may preferably be perfected such that the control diaphragm stop is configured as an at least essentially circular control crater, especially valve crater (valve seat), with an at least essentially circular flow opening and/or the control diaphragm has an at least essentially circular configuration. Circular configurations of both the control crater and of the control diaphragm are configurations that can be made possible in a mechanically especially simple manner. In particular, mechanical stresses, which would occur at corners and/or edges, can be avoided by such a circular configuration. The service life of a valve module according to the present invention can be prolonged as a result.

A valve module according to the present invention may also be configured such that the control element has a preferably actuatable control valve for admitting the control fluid to the control element. Such a preferably actuatable control valve makes it possible, in particular, to admit a settable control pressure of control fluid to the control element, preferably to the control chamber. An especially patient-adapted setting of a valve module according to the present invention, especially of the expiratory limit pressure that can be provided, can be made possible in this manner.

Moreover, provisions may be made in the valve module according to the present invention for the first device interface to have an actuatable valve element, the valve element being configured such that it is opened in case the first device interface is arranged at a first counter-device interface and is otherwise closed. In the case of a valve module that is arranged at a counter-device interface of a ventilator, an expiratory limit pressure can be provided by the ventilator. This can be made possible in an especially simple manner by an actuatable valve element that is opened when the valve module according to the present invention is arranged at the ventilator. This has especially the advantage that, for example, a change in the expiratory limit pressure to be provided can be carried out by a ventilator in an especially simple manner, especially as a function of a monitoring of the entire ventilation process of the patient.

Further, provisions may also be made in the valve module according to the present invention for the valve module to have a data element for storing data, especially ventilation parameters of a ventilation of a patient and/or of ventilation target variables indicating the ventilation process, and a wired and/or wireless data interface connected to the data element in a data-communicating manner for receiving and/or outputting the data. As was described above, it can be made possible by a valve module according to the present invention in an especially simple manner that an exchange can take place between different ventilators. It can be made possible, in particular, by such a data element, to which data of the ventilation process can be sent via a data interface, that the data pertaining to the ventilation process can also be made available to the second ventilator. An especially continuous and constant provision of the ventilation process, especially with constant and/or at least essentially unchanged ventilation parameters, even over a plurality of ventilators, can be made possible in this manner for the patient. The data interface is provided at the valve module.

The object is accomplished according to a second aspect of the present invention by a ventilation tube device, i.e., a tube system, for ventilating a patient by a ventilation system, having an especially at least essentially Y-shaped, continuously hollow ventilation tube element with a patient end for providing breathing air to the patient and for removing exhaled air of the patient, with an inhalation end and with an exhalation end, wherein the inhalation end has a second device interface for fluid-tight connection to a second counter-device interface of an inhalation port of a ventilator of the ventilation system for providing breathing air, and the exhalation end has a counter-tube interface. A ventilation tube device according to the present invention is characterized in that a valve module according to the first aspect of the present invention is arranged at the counter-tube interface for removing exhaled air. All the advantages that were described in reference to a valve module according to the first aspect of the present invention may thus also be provided by a ventilation tube device according to the second aspect of the present invention, which has such a valve module. In particular, complete ventilation of the patient, arriving from a ventilator, can be provided by a ventilation tube device according to the present invention. The ventilation tube device according to the present invention has for this purpose especially a ventilation tube element, which may have an essentially Y-shaped configuration. This Y-shaped configuration makes it possible, in particular, to arrange an inhalation end of the ventilation tube element at an inhalation port of the ventilator for providing breathing air for the patient. This breathing air is sent through the ventilation tube element to the patient and is fed to the lungs of the patient there. Exhaled air, which is again returned to the ventilator via an exhalation end of the ventilation tube element, at which the valve module according to the present invention according to the first aspect of the present invention is arranged, will subsequently come from the lungs.

An inhalation end is preferably a device-side exhalation tube port at the ventilation tube device, i.e., the tube system. The patient end is a patient-side tube port.

Further, provisions may be made in the ventilation tube device according to the present invention for the second device interface to be arranged detachably at the inhalation end of the ventilation tube element. The second device interface represents the inhalation boundary interface between the ventilation tube element and the ventilator. It can be made possible, in particular, by the detachable arrangement of the second device interface that, for example, different ventilation tube elements can be used with the same ventilation interface. Conversely, it can also be made possible that by changing the second device interface, the same ventilation tube element is configured for use with different ventilators.

A ventilator according to the present invention may also be perfected such that the second device interface has a nonreturn valve, which makes possible a breathing flow of breathing air into the ventilation tube element. In particular, a nonreturn valve makes possible in the sense of the present invention a flow of a fluid in one direction, and a flow of the fluid in the opposite direction is blocked by the nonreturn valve. It should be ensured especially in case of Y-shaped ventilation tube elements that exhaled air is also fed to the exhalation end of the ventilation tube element. By arranging a nonreturn valve at the inhalation end of the ventilation tube element, made possible by the second device interface, this can be made possible in an especially simple and reliable manner.

According to a third aspect of the present invention, the object is accomplished by a ventilator for ventilating a patient, having an inhalation port for providing breathing air for the patient and an exhalation port for removing exhaled air from the patient. A ventilator according to the present invention is characterized in that the inhalation port has a second counter-device interface for fluid-tight connection to a second device interface of a ventilation tube device according to the second aspect of the present invention and the exhalation port has a first counter-device interface for fluid-tight connection to a first device interface of a ventilation tube device according to the second aspect of the present invention and/or of a valve module according to the first aspect of the present invention. It can be ensured in this manner that a ventilator according to the present invention according to the third aspect of the present invention can be used with a ventilation tube device according to the present invention according to the second aspect of the present invention and/or with a valve module according to the present invention according to the first aspect of the present invention. A ventilator according to the present invention consequently has all the advantages that were already described in detail in connection with the ventilation tube device according to the present invention according to the second aspect of the present invention and/or in connection with a valve module according to the present invention according to the first aspect of the present invention.

Moreover, provisions may be made in a ventilator according to the present invention for the first counter-device interface to have a control valve interface for actuating a control valve of the valve module. Admission of a control pressure of the control fluid to the control element can be made possible by the control valve of the valve module. It can thus be made possible by such a control valve interface of the first counter-device interface that the admission of the control fluid to the control element can be performed by the ventilator. An especially patient-specific setting of the minimum exhalation pressure provided by the valve module according to the present invention, especially of the expiratory limit pressure, can be made possible in this manner.

A ventilator according to the present invention may especially preferably be perfected such that the control valve interface has a control pressure sensor for determining a control pressure of a control fluid in the control element of the valve module. This offers, on the one hand, the advantage that when filling the control element with the control fluid, the filling pressure and hence the control pressure of the control fluid in the control element can be monitored. Moreover, the control pressure sensor can also be used to detect or to read the control pressure of the control fluid, which is set in the control element, especially if a ventilation tube element with a valve module according to the present invention is arranged, for example, after changing the ventilator used, at the counter-device interface of the ventilator according to the present invention. The expiratory limit pressure in the valve module according to the present invention can be inferred by analyzing these measured data, which makes it possible to start the ventilation process by the ventilator according to the present invention with the same setting in terms of the expiratory limit pressure. In particular, the positive end-expiratory pressure set specifically for the patient can especially be maintained in this manner even after the ventilator used has been changed.

Moreover, a ventilator according to the present invention may be configured such that the ventilator has a wired and/or wireless counter-data interface for receiving data of a data interface of the valve module and/or for sending data to a data interface of the valve module. In particular, a data exchange can be made possible in this manner between the ventilator and the valve module. A data transfer, especially also between a plurality of ventilators, can be made possible in this manner. The counter-data interface is provided at the ventilator.

A ventilator according to the present invention may also be configured such that the ventilator has an input element for triggering a start of establishing and/or severing a fluid-communicating connection to a ventilation tube device at the inhalation port and/or at the exhalation port and/or for triggering a start of establishing and/or severing a fluid-communicating connection to a valve module at the exhalation port. Such recognition of a triggering of the establishment and/or severing by actuating the input element at both the inhalation port and the exhalation port makes it possible, in particular, that the correspondingly needed actions therefor can be taken. For example, the start of severing the fluid-communicating connection to the valve module may require that the corresponding control pressure of control fluid be admitted to the control element. Transmission of data to be performed between the data interface and the counter-data interface or vice versa may also be initiated by such actuation of the input element.

According to a fourth aspect of the present invention, the object is accomplished by a ventilation system for ventilating a patient, having a ventilator and a ventilation tube device connected to the ventilator in a fluid-communicating manner. A ventilation system according to the present invention is characterized in that the ventilator is configured according to the third aspect of the present invention and the ventilation tube device is configured according to the second aspect of the present invention. All the advantages that were described in reference to a ventilator according to the present invention according to the third aspect of the present invention and in reference to a ventilation tube device according to the present invention according to the second aspect of the present invention can thus also be provided by a ventilation system according to the present invention according to the fourth aspect of the present invention. Since a ventilation tube device according to the present invention according to the second aspect of the present invention has a valve module according to the present invention according to the first aspect of the present invention, it is thus also possible, in particular, to provide all the advantages that were described in reference to a valve module according to the first aspect of the present invention by a ventilation system according to the present invention according to the fourth aspect of the present invention.

According to a fifth aspect of the present invention, the object is accomplished by a process for severing a fluid-communicating connection between a first device interface of a ventilation tube device and a first counter-device interface of an exhalation port of a ventilator of a ventilation system according to the fourth aspect of the present invention. A process according to the present invention for severing a fluid-communicating connection is characterized by the following steps:
  a) Reception of a triggering of a start of the severing,
  b) determination of a control pressure for a control fluid, wherein an expiratory limit pressure is set by the control pressure in the valve module,
  c) filling of the control element of the valve module of the ventilation tube device with a control fluid, the control fluid having the control pressure determined in step b), and
  d) severing the fluid-communicating connection by separating the first device interface and the first counter-device interface.

A process according to the present invention is carried out by a ventilator of a ventilation system according to the fourth aspect of the present invention. All the advantages that were described in connection with a ventilation system according to the fourth aspect of the present invention and hence also all the advantages that were described in reference to a valve module according to the first aspect of the present invention, in reference to a ventilation tube device according to the second aspect of the present invention as well as in reference to a ventilator according to the third aspect of the present invention can thus also be provided by a process for severing a fluid-communicating connection according to the fifth aspect of the present invention.

A fluid-communicating connection between a first device interface of a ventilation tube device and a first counter-device interface of an exhalation port of a ventilator of a ventilation system can be severed by a process according to the present invention. In particular, a valve module according to the present invention is arranged at the device of the first device interface of the ventilation tube device. A triggering of the start of a severing is received in a first step a) of the process according to the present invention. This may be, for example, a separation of a fixing device of the ventilation tube element at the ventilator or an actuation of an input element of the ventilator. A control pressure for the control fluid in the valve module according to the present invention is determined subsequently or at the same time, and an expiratory limit pressure is especially set by this control pressure in the valve module. In other words, a control pressure for the control fluid can, for example, preferably be calculated from the expiratory limit pressure used in the ventilator. This calculation may be made by a computer of the ventilator. The same expiratory limit pressure shall be provided by precisely this control pressure in the valve module according to the present invention and in the ventilation tube device according to the present invention after the separation from the ventilator. To ensure this, the control element of the valve module of the ventilation tube device is filled with a control fluid in the next step c), the control fluid especially having the control pressure determined in step b). It can be ensured in this manner that the expiratory limit pressure can be provided for the exhaled air of the patient even after separating the valve module and hence the ventilation tube device from the ventilator. The actual severing of the fluid-communicating connection of the first device interface and the first counter-device interface is then carried out in the last step d). After carrying out step d) of a process according to the present invention, there is consequently no fluid-communicating connection between the exhalation end of the ventilation tube device and the ventilator. The severing of the fluid-communicating connection has been concluded.

A process according to the present invention may preferably be perfected such that the triggering is received by an input element of the ventilator in step a). Such an input element may be, for example, a key, a slider control or the like. An input via a touch-sensitive display device, for example, a touch display, is also possible. The imminent occurrence of severing of the ventilation tube device from the ventilator can thus be signaled in an especially simple manner by such an input element.

Moreover, provisions may be made in the process according to the present invention for the transmission of data, especially ventilation parameters of the ventilation of the patient, and/or ventilation target variables indicating the process to a data element of the valve module in a wired and/or wireless manner from a counter-data interface of the ventilator via a data interface of the valve module. This may especially preferably be carried out subsequent to step a), for example, during steps b) and c). It can be made possible hereby, in particular, that ventilation parameters of the ventilation of the patient and/or ventilation target variables indicating the ventilation process can be stored, for example, in a data element of the valve module. Transmission of these data from a first ventilator to a second ventilator can be made possible in this manner in an especially simple manner. A continuous and/or at least essentially continuous continuation of the ventilation process with another, second ventilator, especially with the use of the same ventilation parameters and/or ventilation target variables, can be made possible in this manner in an especially simple manner.

A process according to the present invention may especially preferably be configured, furthermore, such that an expiratory limit pressure of the ventilation of the patient is determined in step b) and the control pressure of the control fluid is determined from the determined expiratory limit pressure. The expiratory limit pressure of the ventilation of the patient pertains especially to the positive end-expiratory pressure of the breathing of the patient, which often forms an essential ventilation parameter of the ventilation process. It can be ensured by determining this expiratory limit pressure and by correspondingly determining or setting the control pressure of the control fluid that exhalation by the patient can also be continued after separating the valve module from the ventilator by taking this expiratory limit pressure into account.

A process according to the present invention may also be configured such that removal of exhaled air of the patient through the exhalation port of the ventilator is ended after step c). After carrying out step c) of the process according to the present invention for severing a fluid-communicating connection, the control element is filled with the corresponding control pressure of control fluid. The pressure-limiting element of the valve module according to the present invention is ready for use in this manner. Removal of exhaled air of the patient through the exhalation port of the ventilator can thus be set without limitation of the ventilation process of the patient and especially as a preparation for the actual severing in step d), because continuous provision of the expiratory limit pressure can be made possible by the pressure-limiting element.

According to a sixth aspect of the present invention, the object is accomplished by a process for establishing a fluid-communicating connection between a first device interface of a ventilation tube device and a first counter-device interface of an exhalation port to a ventilator of a ventilation system according to the fourth aspect of the present invention. A process according to the present invention for establishing a fluid-communicating connection is characterized by the following steps:

w) Arrangement of the first device interface at the first counter-device interface, x) determination of the control pressure of the control fluid in the control element of the valve module of the ventilation tube device, y) determination of the expiratory limit pressure based on the control pressure determined in step x), and z) establishing the fluid-communicating connection and starting the removal of exhaled air of the patient through the exhalation port of the ventilator with the use of the expiratory limit pressure determined in step y).

The process according to the present invention according to the sixth aspect of the present invention represents a process opposite the process according to the fifth aspect of the present invention. Again, a process according to the present invention for establishing a fluid-communicating connection according to the sixth aspect of the present invention can be carried out by a ventilation system according to the present invention according to the fourth aspect of the present invention. A process according to the present invention for establishing a fluid-communicating connection according to the sixth aspect of the present invention may have in this manner all the advantages that were described in connection with a ventilation system according to the present invention according to the fourth aspect of the present invention. Moreover, a process according to the present invention for establishing a fluid-communicating connection according to the sixth aspect of the present invention can thus also have all the advantages that were described in detail in reference to a valve module according to the present invention according to the first aspect of the present invention, in reference to a ventilation tube device according to the present invention according to the second aspect of the present invention as well as in reference to a ventilator according to the present invention according to the third aspect of the present invention.

In a first step w) of a process according to the present invention for establishing a fluid-communicating connection, the first device interface is arranged at the first counter-device interface. It could thus be possible, in principle, to remove exhaled air through the ventilator again already after this establishing a connection in step w) of a process according to the present invention. The remaining steps of the process according to the present invention are used especially to ensure correct removal of this exhaled air and the actual establishment of the fluid-communicating connection. Thus, a control pressure, which the control fluid has in the control element of the valve module of the ventilation tube device, is determined in the next step x) of a process according to the present invention. This control pressure was, in turn, set preferably in a process according to the present invention according to the fifth aspect of the present invention such that an expiratory limit pressure is set by it for the exhalation flow of the exhaled air of the patient such that this limit pressure is exactly equal or at least similar to the expiratory limit pressure that was provided in the starting ventilator. It is made possible in the next step y) by this determination of the control pressure to determine precisely this expiratory limit pressure on the basis of the control pressure determined in step x). This may be carried out, for example, by a computer of the ventilator. After establishing the fluid-communicating connection, removal of the exhaled air of the patient through the exhalation port of the ventilator is begun in the last step z) of a process according to the present invention, using the expiratory limit pressure determined in step y). It can be made possible in this manner, in particular, that, starting from a first ventilator, the expiratory limit pressure is transferred to the ventilation tube device, especially the valve module of the ventilation tube device, and it is then transferred again from the valve module of the ventilation tube to the second ventilator of the ventilation system. It is possible to ensure a continuous provision of the same expiratory limit pressure or of an at least essentially constant expiratory limit pressure in this manner.

A process according to the present invention may also be configured such that data, especially ventilation parameters of the ventilation of the patient and/or ventilation target variables indicating the ventilation process, are transmitted before step z) from a data element of the valve module via a data interface of the valve module to a counter-data interface of the ventilator in a wired and/or wireless manner. It can be made possible in this manner, in particular, that these data, which were preferably transmitted from a first ventilator to the valve module, will also be passed on to the next following ventilator. Since these data comprise especially ventilation parameters of the ventilation of the patient and/or ventilation target variables indicating the ventilation process, an especially smooth continuation of the ventilation process of the patient can be made possible in this manner with the use of the transmitted ventilation parameters and/or ventilation target variables.

The processes according to the fifth and sixth aspects advantageously form one unit and accomplish one and the same object, namely, to improve the severing and establishment of fluid-communicating connections. The process steps according to the fifth and sixth aspects may thus be combined with one another in order to establish and then sever a fluid-communicating connection.

Additional measures improving the present invention appear from the following description of exemplary embodiments of the present invention, which are shown in the figures. All the features and/or advantages appearing from the claims, from the description and from the drawings, including design details and arrangements in space, may be essential for the present invention both in themselves and in the different combinations. Elements having the same function and mode of operation are designated by the same reference numbers in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
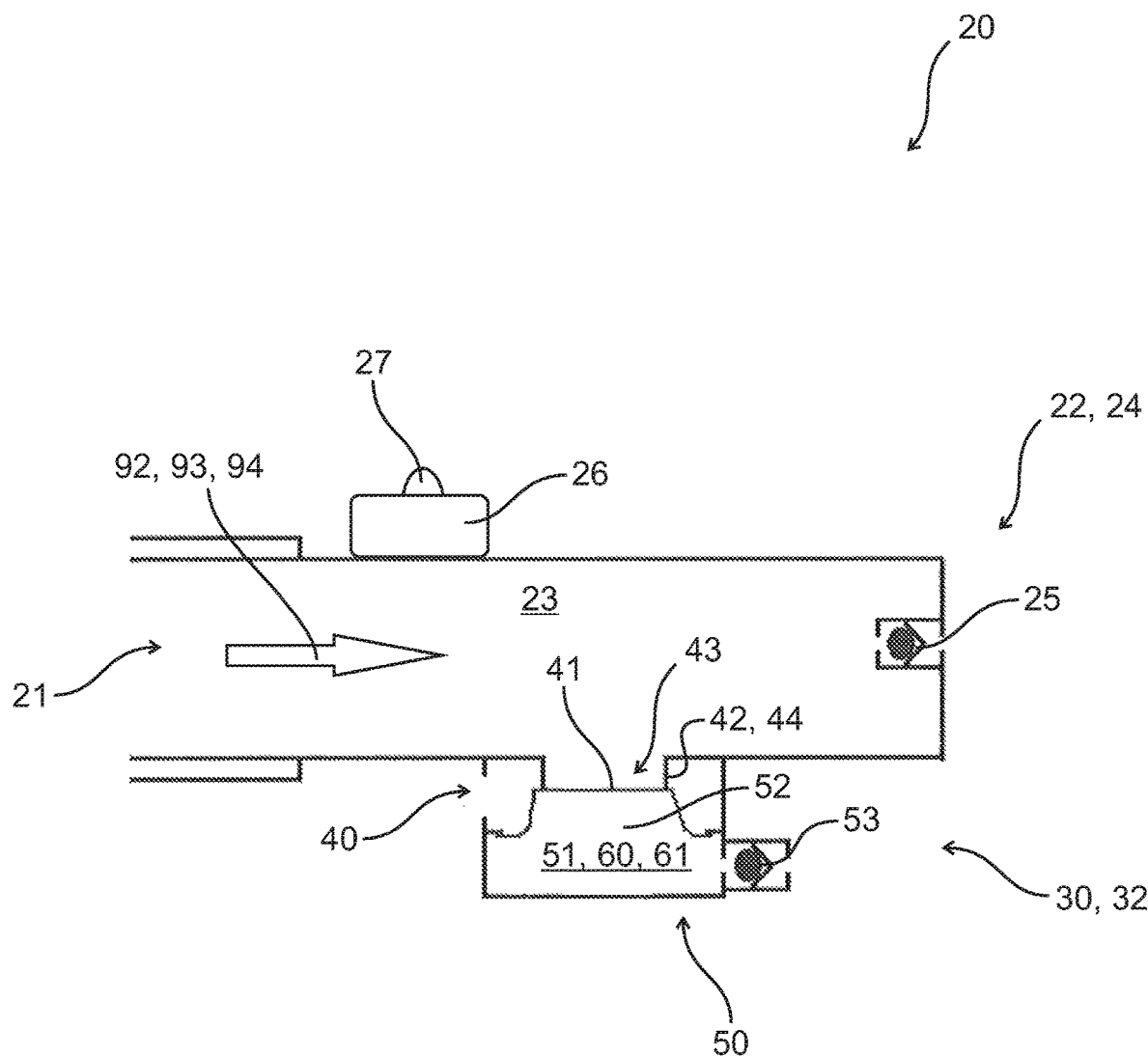
FIG. 1 is a schematic view of a valve module according to the present invention with a control element in the blocking position thereof.
Figure 2:
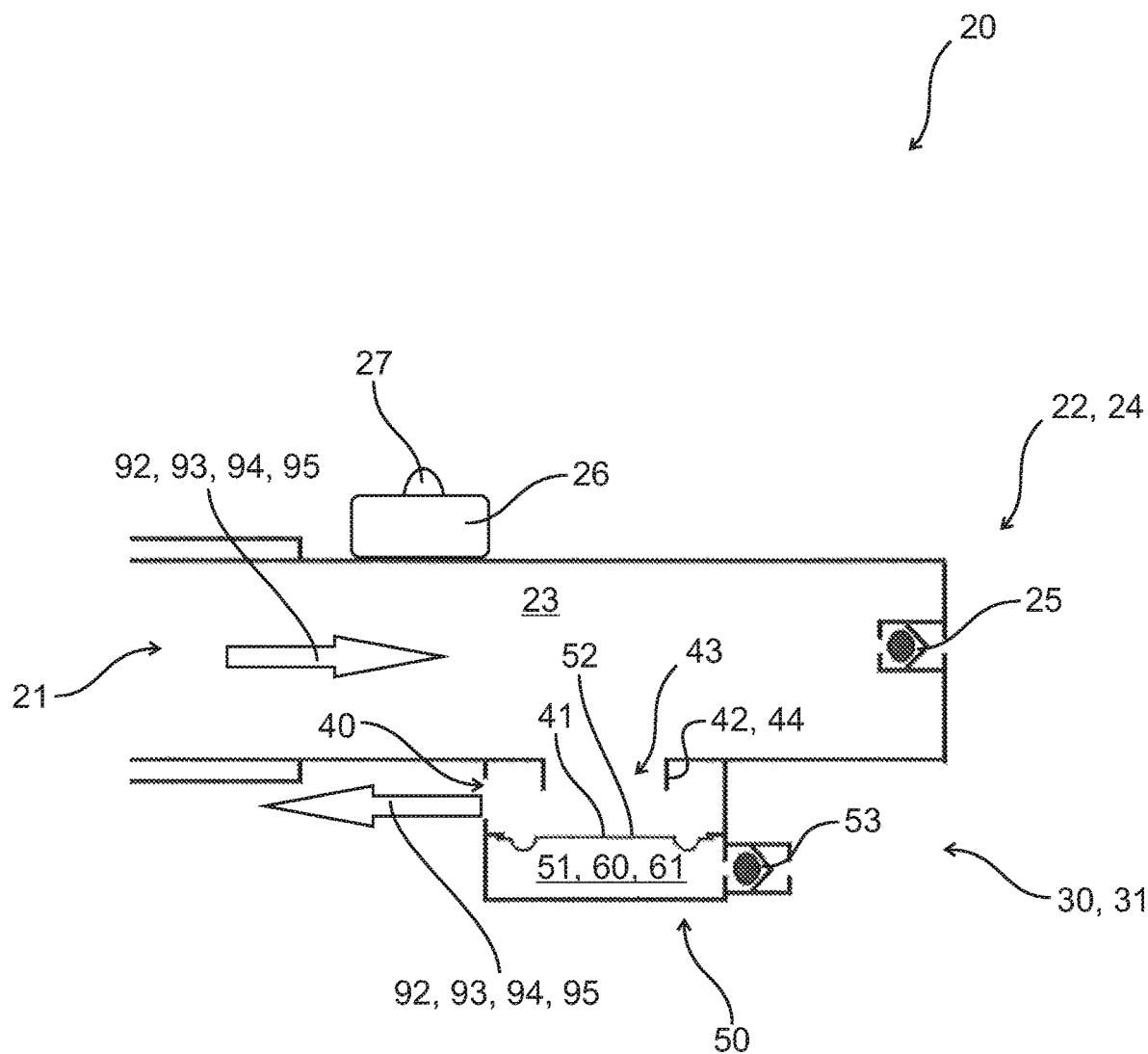
FIG. 2 is a schematic view of a valve module according to the present invention with a control element in the flow position thereof.

Referring to the drawings, FIGS. 1 and 2 show a possible type of configuration of a valve module 20 according to the present invention. The pressure-limiting element 30 of the valve module 20 is shown, in particular, in its blocking position 32 in FIG. 1 and in its flow position 31 in FIG. 2. The two figures will be described together below, and details will always be discussed separately. The valve module 20 according to the present invention is intended for arrangement at an exhalation end 13 of a ventilation tube element 11 of a ventilation tube device 10. The valve module 20 according to the present invention has especially a tube interface 21 for this purpose. The valve module 20 according to the present invention represents especially an intermediate element between the ventilation tube device 10 and a ventilator 110 (not shown in FIGS. 1 and 2). The valve module 20 has a first device interface 22 for this purpose on a valve module side located especially opposite the tube interface 21. Provisions are made, in particular, in the state in which the valve module 20 is connected to the ventilator 110, especially to an exhalation port 113 (FIG. 3) of the ventilator 110, for a valve element 25 to be actuated such that exhaled air 92 can flow with an exhalation pressure 94 through the valve module 20 in an exhalation flow 93. In addition to the arrangement at the ventilator 110, the valve module 20 according to the present invention is, however, provided especially for also making possible a transfer to another ventilator 110. Such a transfer comprises especially separation from a ventilator 110, as it is shown in a process shown in FIG. 4, as well as a reconnection or establishment of a fluid-communicating connection to another ventilator 110, as it is shown in the process shown in FIG. 5.

A valve module 20 according to the present invention is configured for these cases such that it is also able to continue to maintain an expiratory limit pressure 95 of the exhaled air 92. This will be described below. Thus, the valve module 20 according to the present invention has in its exhalation valve section 24 especially a pressure-limiting element 30. This pressure-limiting element 30 comprises especially a control section 40 as well as a control element 50. The control element 50 may preferably have, as shown, a control chamber 51, to which a control fluid 60, having a control pressure 61, can be admitted. A control opening 52 of the control chamber 51 can preferably be closed by a control diaphragm 41 of the control section 40, which said control diaphragm has especially an at least partially flexible configuration. When the control fluid 60, for example, air, is admitted to the control chamber 51, the control diaphragm 41 will now have an arched configuration depending on the control pressure 61. The control section 40 further has, as a counterpiece to the control diaphragm 41, a control diaphragm stop 42. Both the control diaphragm 41 and the control diaphragm stop 42 may preferably have at least essentially circular configurations. Thus, especially the control diaphragm stop 42 may be configured, for example, as a circular control crater (valve seat) 44. As was described, the control pressure 61 of the control fluid 60 is admitted to the control diaphragm 41 through the control chamber 51. At the same time, the control crater 44 encloses a flow opening 43, through which the exhaled air 92 with its exhalation pressure can likewise be admitted to the control diaphragm 41. If the exhalation pressure 94 now exceeds the force that acts on the control diaphragm 41 due to the control pressure 61, the control diaphragm 41 is displaced from the position shown in FIG. 1, in which it blocks the flow opening 43 in the control diaphragm stop 42 in a fluid-tight manner and the pressure-limiting element 30 is thus in its blocking position 32, into the position shown in FIG. 2, in which the control diaphragm 41 releases the flow opening 43 and the pressure-limiting element 30 is thus in its flow position 31. On the whole, the flow opening 43 is thus released depending on the exhalation pressure 94 and the control pressure 61 and the exhaled air 92 or the entire exhalation flow 93 can be discharged from the exhalation valve 24 of the valve module 20. In particular, the control pressure 61 of the control fluid 60 can be set such that a certain expiratory limit pressure 95, starting from which a breathing flow 91 from the valve module 20 is possible, becomes established for the exhaled air 92. This expiratory limit pressure 95 may especially preferably correspond to a positive end-expiratory pressure, which can be set in a patient-dependent manner. To make it now possible to admit the control fluid 60 into the control chamber 51, the control element 50 also has especially a control valve 53. Further, a data element 26 and a wired and/or wireless data interface 27, via which especially data pertaining to the ventilation process can be stored on the data element 26, may also be present in a valve module 20 according to the present invention. Data pertaining to the ventilation process can be transferred in an especially simple manner especially in case of a transfer of the valve module 20 or of the ventilation tube device 10 from one ventilator 110 to another ventilator 110.

Figure 3:
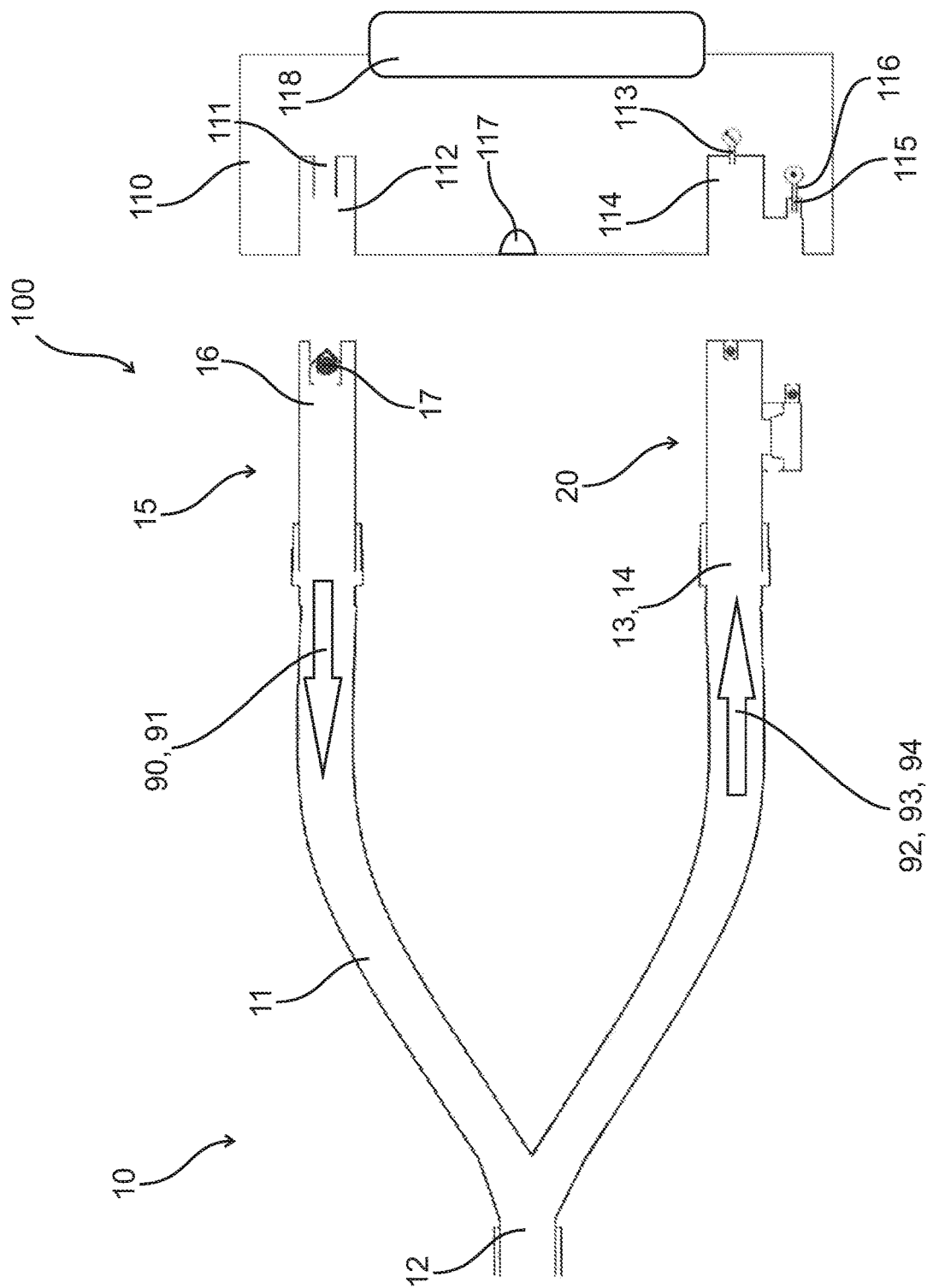
FIG. 3 is a schematic view of a ventilation system according to the present invention.

FIG. 3 shows a ventilation system 100 according to the present invention, having especially a ventilator 110 as well as a ventilation tube device 10. The ventilation tube device 10 is configured with its patient end 12 for providing breathing air 90 with a breathing flow 91 as well as for removing exhaled air 92 with an exhalation flow 93 for the patient (not shown). The ventilation tube element 11 used especially preferably has a Y-shaped configuration. A second device interface 16, which may especially be arranged reversibly, is arranged at an inhalation end 15. It can be ensured by means of a nonreturn valve 17 that only a breathing flow 91 can flow through the inhalation end 15 even when the inhalation end 15 is separated. The inhalation end 15 further has a second device interface 16, via which it can be made possible to arrange the inhalation end 15 at a second counter-device interface 112 of an inhalation port 111 of the ventilator 107. A valve module 20 according to the present invention, as it is described, for example, in FIGS. 1 and 2, is arranged at a counter-tube interface 14 at an exhalation end 13 of the ventilation tube element 11. The individual elements of the valve module 20 according to the present invention are not provided with reference numbers for the sake of increasing clarity. The first device interface 22 of the valve module 20 may be arranged at a first counter-device interface 114 at an exhalation port 113. At the same time, a control valve interface 115 for interacting with a control valve 53 of the control element 50 of the valve module is arranged at the first counter-device interface 114. In particular, admission of control fluid 60 with a control pressure 61 to the control element 50 can be made possible through such a control valve interface 115. At the same time, the control valve interface 115 may have a control pressure sensor 116, by which reading of the control pressure 61 present in the control element 50 can be made possible. It is possible in this manner especially to determine and identify an expiratory limit pressure 95 set in the valve module 20, for example, by a computer (comprised of one or more processors and associated memory) of the ventilator 110. It can be made possible in this manner to continue a ventilation process by the ventilator 110 with the same or at least essentially the same expiratory limit pressure 95. Another element of a ventilator 110 according to the present invention may represent an input element 118, via which it is possible, for example, to trigger an imminent severing or establishment of a fluid-communicating connection of the ventilator 110 to a ventilation tube device 10. To make it possible to transmit especially data concerning the ventilation process of the patient, provisions may further be made for the ventilator 110 to have a counter-data interface 117. Together with a data interface 27 of the valve module 20, data concerning this ventilation process can be transmitted and/or exchanged via this counter-data interface to a data element 26 of the valve module 20.

Figure 4:
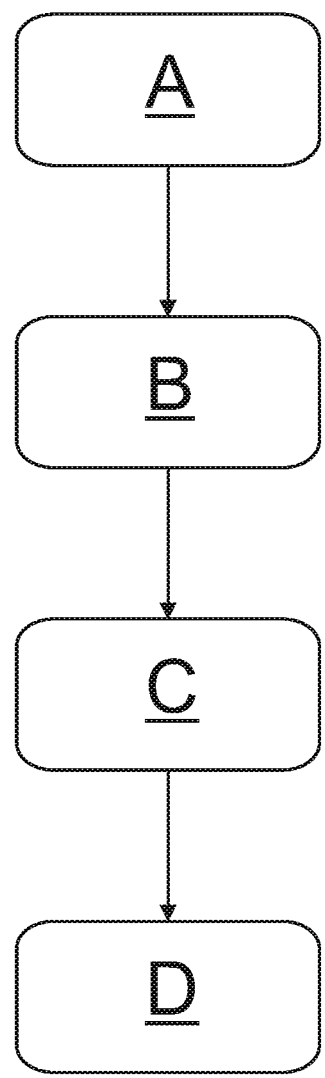
FIG. 4 is a flow diagram of a process according to the present invention for severing a fluid-communicating connection.

FIG. 4 schematically shows a process according to the present invention for severing a fluid-communicating connection between a first device interface 22 of a ventilation tube device 10 and a first counter-device interface 114 of an exhalation port 113 of a ventilator 110 of a ventilation system 100. The particular devices needed are not shown. Steps a) through d) are designated by capital letters A through D in FIG. 4. Thus, the start of the severing of the fluid-communicating connection is received in step a) of a process according to the present invention, designated by A in FIG. 4. This may be carried out, for example, by an input element 118 of the ventilator 110. A control pressure 61 for a control fluid 60 is determined in the next step b) of a process according to the present invention, designated by B in FIG. 4. Especially an expiratory limit pressure 95 is set in the valve module 20 by this control pressure 61. It can be made possible in this manner to maintain the expiratory limit pressure 95, as it is used in the corresponding ventilator 110. In particular, an expiratory limit pressure 95 of the ventilation of the patient, which is currently set, can be determined in this manner, and the control pressure 61 of the control fluid 60 can be determined from this determined limit pressure. The control element 50 of the valve module 20 of the ventilation tube device 10 is filled with the control fluid 60 in the next step c) of the process according to the present invention, designated by C in FIG. 4. This filling is carried out, in particular, such that the control fluid 60 has the control pressure 61 determined in step b). The actual severing and hence the cutting of the fluid-communicating connection between the first device interface 22 and the first counter-device interface 114 is carried out in the last step d) of a process according to the present invention, designated by D in FIG. 4. In particular, removal of exhaled air 92 of the patient through the exhalation port 113 of the ventilator 110 may already have been ended before. In particular, to transmit data concerning the ventilation process of the patient, provisions may further be made for transmitting data concerning this ventilation process to a data element 26 of the valve module 20 from a counter-data interface 117 of the ventilator 110 via a data interface 27 of the valve module 20. This may be carried out especially in a wired and/or wireless manner via a corresponding data interface 27.

Figure 5:
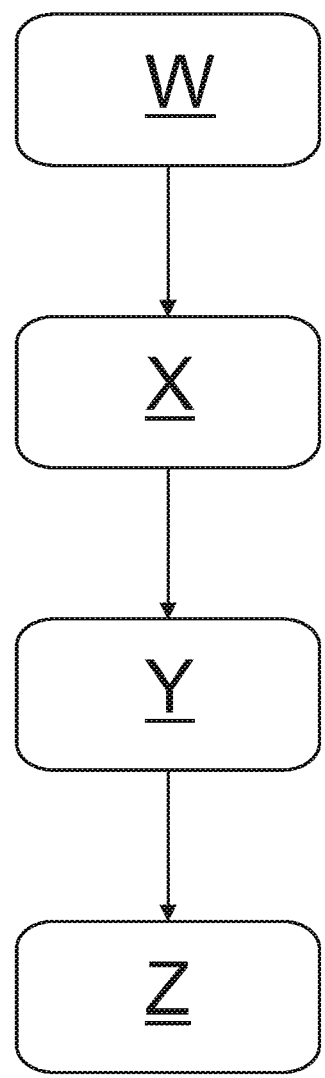
FIG. 5 is a flow diagram of a process according to the present invention for establishing a fluid-communicating connection.

FIG. 5 shows the opposite process for establishing a fluid-communicating connection between a first device interface 22 of a ventilation tube device 10 and a first counter-device interface 114 of an exhalation port 113 of a ventilator 110 of a ventilation system 100. The devices used are not shown here, either. The individual steps w) through z) are designated by capital letters W through Z in FIG. 5. Thus, the first device interface 22 is arranged at the first counter-device interface 114 in the first step w) of a process according to the present invention, designated by W in FIG. 5. Removal of exhaled air 92 through the ventilator 110 of the ventilation 100 would, in principle, already be possible hereby. In order to improve this and especially to provide an expiratory limit pressure 95 for this removal of the exhaled air 92, a control pressure 61 of the control fluid 60 in the control element 50 of the valve module 20 of the ventilation tube device 10 is determined in the next step x) of a process according to the present invention, designated by X in FIG. 5. The control pressure 61 thus determined is decisive for the expiratory limit pressure 95 that is set in the valve module 20 of the ventilation tube device 10. This is used in the next step y) of a process according to the present invention, designated by Y in FIG. 5, to determine this expiratory limit pressure 95 on the basis of the control pressure 61 determined in step x). The actual establishment of the fluid-communicating connection is carried out and removal of exhaled air 92 of the patient through the exhalation port 113 of the ventilator 110 is started in the last step z) of a process according to the present invention, designated by Z in FIG. 5, and the expiratory limit pressure 95 determined in step y) may preferably be used. It can be made possible in this manner to carry out the ventilation process of the patient especially uniformly and continuously. In particular, provisions may be made for further improving a process according to the present invention for transmitting data, especially ventilation parameters of the ventilation of the patient and/or ventilation target variables indicating the ventilation process from a data element 26 of the valve module 20 already before step z). This may be carried out in a wired or wireless manner especially via a data interface 27 of the valve module 20 to a counter-data interface 117 of the ventilator 110. It can be ensured in this manner to continue the ventilation process of the patient even better and more uniformly.

While specific embodiments of the invention have been shown and described in detail to illustrate the application of the principles of the invention, it will be understood that the invention may be embodied otherwise without departing from such principles.

LIST OF REFERENCE NUMBERS

| | |
|---|---|
| 10 | Ventilation tube device |
| 11 | Ventilation tube element |
| 12 | Patient end |
| 13 | Exhalation end |
| 14 | Counter-tube interface |
| 15 | Inhalation end |
| 16 | Second device interface |
| 17 | Nonreturn valve |
| 20 | Valve module |
| 21 | Tube interface |
| 22 | First device interface |
| 23 | Module space |
| 24 | Exhalation valve section |
| 25 | Valve element |
| 26 | Data element |
| 27 | Data interface |
| 30 | Pressure-limiting element |
| 31 | Flow position |
| 32 | Blocking position |
| 40 | Control section |
| 41 | Control diaphragm |
| 42 | Control diaphragm stop |
| 43 | Flow opening |
| 44 | Control crater |
| 50 | Control element |
| 51 | Control chamber |
| 52 | Control opening |
| 53 | Control valve |
| 60 | Control fluid |
| 61 | Control pressure |
| 90 | Breathing air |
| 91 | Breathing flow |
| 92 | Exhaled air |
| 93 | Exhalation flow |
| 94 | Exhalation pressure |
| 95 | Expiratory limit pressure |
| 100 | Ventilation system |
| 110 | Ventilator |
| 111 | Inhalation port |
| 112 | Second counter-device interface |
| 113 | Exhalation port |
| 114 | First counter-device interface |
| 115 | Control valve interface |
| 116 | Control pressure sensor |
| 117 | Counter-data interface |
| 118 | Input element |

What is claimed is:

1. A valve module for a ventilation system for ventilating a patient, the valve module comprising:
a tube interface for fluid-tight connection to a counter-tube interface of an exhalation end of a ventilation tube element;
a device interface for fluid-tight connection to a counter-device interface of an exhalation port of a ventilator of the ventilation system, wherein the tube interface and the device interface are fluid-communicatingly connected by a module space, wherein:
the device interface comprises an exhalation valve section for at least partially providing an exhalation flow of exhaled air with an exhalation pressure, the exhaled air arriving from the tube interface and flowing through the module space;
the exhalation valve section includes a pressure-limiting element comprising a control section and a control element, wherein a control fluid with a control pressure is admitted to the control element;
the control section is functionally connected to the control element and the exhalation pressure of the exhaled air is admitted to the control section; and
the pressure-limiting element is positioned, depending on the control pressure of the control fluid in the control element and depending on the exhalation pressure of the exhaled air, at least into a flow position, in which the pressure-limiting element releases the exhalation flow through the exhalation valve section, and into a blocking position, in which the pressure-limiting element blocks the exhalation flow through the exhalation valve section.

2. A valve module in accordance with claim 1, wherein:
the positioning of the pressure-limiting element in dependence on the exhalation pressure of the exhaled air and on the control pressure of the control fluid is configured such that an expiratory limit pressure can be set for the exhaled air by selecting the control pressure;
the pressure-limiting element is in the blocking position in case of an exhalation pressure lower than the expiratory limit pressure; and
the pressure-limiting element is in the flow position in case of an exhalation pressure higher than the expiratory limit pressure.

3. A valve module in accordance with claim 1, wherein:
the control element comprises a control chamber with a control opening; and
the control section comprises a control diaphragm, which is flexible in at least some sections, and a control diaphragm stop;
the control diaphragm stop has a flow opening for the exhalation flow of the exhaled air;
the control diaphragm fluid-tightly closes the control opening of the control chamber and fluid-tightly blocks the flow opening in the blocking position of the pressure-limiting element; and
the control diaphragm releases the flow opening for the exhalation flow of the exhaled air in the flow position of the pressure-limiting element.

4. A valve module in accordance with claim 3, wherein:
the control diaphragm stop is configured as an at least essentially circular control crater with an at least essentially circular flow opening; or
the control diaphragm has an at least essentially circular configuration; or
the control diaphragm stop is configured as an at least essentially circular control crater with an at least essentially circular flow opening and the control diaphragm has an at least essentially circular configuration.

5. A valve module in accordance with claim 1, wherein the control element has an actuatable control valve for admitting the control fluid to the control element.

6. A valve module in accordance with claim 1, wherein:
the device interface has an actuatable valve element;

the actuatable valve element is configured to be opened if the device interface is arranged at a counter-device interface and is otherwise closed.

7. A valve module in accordance with claim 1, further comprising:
a data element for storing ventilation parameter data of a ventilation of a patient and/or ventilation target variables data indicating the ventilation process; and
a wired and/or wireless data interface data-communicatingly connected to the data element for receiving and/or outputting the data.

8. A ventilation tube device for ventilating a patient by a ventilation system, the ventilation tube device comprising:
a hollow ventilation tube element with a patient end for providing breathing air to the patient and for removing exhaled air of the patient, with an inhalation end and an exhalation end, wherein the exhalation end has a counter-tube interface;
a valve module arranged at the counter-tube interface for removing exhaled air, the valve module comprising: a tube interface for fluid-tight connection to the counter-tube interface and a first device interface for fluid-tight connection to a first counter-device interface of an exhalation port of a ventilator of the ventilation system, wherein the tube interface and the first device interface are fluid-communicatingly connected by a module space, wherein:
the first device interface comprises an exhalation valve section for at least partially providing an exhalation flow of exhaled air with an exhalation pressure, the exhaled air arriving from the tube interface and flowing through the module space;
the exhalation valve section includes a pressure-limiting element comprising a control section and a control element, wherein a control fluid with a control pressure is admitted to the control element;
the control section is functionally connected to the control element and the exhalation pressure of the exhaled air is admitted to the control section;
the pressure-limiting element is positioned, depending on the control pressure of the control fluid in the control element and depending on the exhalation pressure of the exhaled air, at least into a flow position, in which the pressure-limiting element releases the exhalation flow through the exhalation valve section, and into a blocking position, in which the pressure-limiting element blocks the exhalation flow through the exhalation valve section; and
the inhalation end has a second device interface for fluid-tight connection to a second counter-device interface of an inhalation port of the ventilator of the ventilation system for providing breathing air.

9. A ventilation tube device in accordance with claim 8, wherein the second device interface is arranged detachably at the inhalation end of the ventilation tube element.

10. A ventilation tube device in accordance with claim 8, wherein the second device interface comprises a nonreturn valve, which makes possible a breathing flow of breathing air into the ventilation tube element.

11. A ventilator for ventilating a patient, the ventilator comprising:
an exhalation port for removing exhaled air from the patient, wherein the exhalation port comprises a first counter-device interface for a fluid-tight connection to a first device interface of a ventilation tube device comprising a hollow ventilation tube element with a patient end for providing breathing air to the patient and for removing exhaled air of the patient, with an inhalation end and an exhalation end, wherein the exhalation end has a counter-tube interface; and a valve module arranged at the counter-tube interface for removing exhaled air, the valve module comprising: a tube interface for fluid-tight connection to the counter-tube interface and the first device interface for fluid-tight connection to the first counter-device interface, wherein the tube interface and the first device interface are fluid-communicatingly connected by a module space, wherein: the first device interface comprises an exhalation valve section for at least partially providing an exhalation flow of exhaled air with an exhalation pressure, the exhaled air arriving from the tube interface and flowing through the module space; the exhalation valve section includes a pressure-limiting element comprising a control section and a control element, wherein a control fluid with a control pressure is admitted to the control element by the exhalation port of the ventilator; the control section is functionally connected to the control element and the exhalation pressure of the exhaled air is admitted to the control section; the pressure-limiting element is positioned, depending on the control pressure of the control fluid in the control element and depending on the exhalation pressure of the exhaled air, at least into a flow position, in which the pressure-limiting element releases the exhalation flow through the exhalation valve section, and into a blocking position, in which the pressure-limiting element blocks the exhalation flow through the exhalation valve section; and the inhalation end has a second device interface; and
an inhalation port for providing breathing air for the patient, wherein the inhalation port comprises a second counter-device interface for a fluid-tight connection to the second device interface of the ventilation tube device for providing breathing air.

12. A ventilator in accordance with claim 11, wherein:
the control element has an actuatable control valve for admitting the control fluid to the control element; and
the first counter-device interface has a control valve interface for actuating a control valve of the valve module.

13. A ventilator in accordance with claim 12, wherein the control valve interface has a control pressure sensor for determining a control pressure of a control fluid in the control element of the valve module.

14. A ventilator in accordance with claim 11, further comprising a wired and/or wireless counter-data interface for receiving data and/or for outputting data to a data interface of the valve module.

15. A ventilator in accordance with claim 11, further comprising an input element for triggering a start of the establishment and/or severing of a fluid-communicating connection to the ventilation tube device at the inhalation and/or exhalation port and/or for triggering a start of the establishment and/or severing of a fluid-communicating connection to a valve module at the exhalation port.

16. A ventilation system for ventilating a patient, the ventilation system comprising:
a ventilation tube device comprising:
a hollow ventilation tube element with a patient end for providing breathing air to the patient and for removing exhaled air of the patient, with an inhalation end and an exhalation end, wherein the exhalation end has a counter-tube interface; and a valve module arranged at the counter-tube interface for removing exhaled air, the valve module comprising: a tube interface for fluid-tight connection to the counter-tube interface and a first device interface for fluid-tight connection to a first counter-device interface of an exhalation port of a ventilator of the ventilation system, wherein the tube interface and the first device interface are fluid-communicatingly connected by a module space, wherein:

the first device interface comprises an exhalation valve section for at least partially providing an exhalation flow of exhaled air with an exhalation pressure, the exhaled air arriving from the tube interface and flowing through the module space;

the exhalation valve section includes a pressure-limiting element comprising a control section and a control element, wherein a control fluid with a control pressure is admitted to the control element;

the control section is functionally connected to the control element and the exhalation pressure of the exhaled air is admitted to the control section;

the pressure-limiting element is positioned, depending on the control pressure of the control fluid in the control element and depending on the exhalation pressure of the exhaled air, at least into a flow position, in which the pressure-limiting element releases the exhalation flow through the exhalation valve section, and into a blocking position, in which the pressure-limiting element blocks the exhalation flow through the exhalation valve section; and the inhalation end has a second device interface for fluid-tight connection to a second counter-device interface of an inhalation port of the ventilator of the ventilation system for providing breathing air; and a ventilator comprising:

an exhalation port for removing exhaled air from the patient, wherein the exhalation port has a counter-device interface for a fluid-tight connection to the first device interface of the ventilation tube device; and an inhalation port for providing breathing air for the patient, wherein the inhalation port comprises a second counter-device interface for a fluid-tight connection to the second device interface of the ventilation tube device for providing breathing air.

17. A process for severing a fluid-communicating connection between a device interface of a ventilation tube device and a counter-device interface of an exhalation port of a ventilator of a ventilation system, the process comprising:

providing the ventilation system, wherein the provided ventilation system comprises a ventilation tube device comprising: a hollow ventilation tube element with a patient end for providing breathing air to the patient and for removing exhaled air of the patient, with an inhalation end and an exhalation end, wherein the exhalation end has a counter-tube interface; and a valve module arranged at the counter-tube interface for removing exhaled air, the valve module comprising: a tube interface for fluid-tight connection to the counter-tube interface and a first device interface for fluid-tight connection to a first counter-device interface of an exhalation port of a ventilator of the ventilation system, wherein the tube interface and the first device interface are fluid-communicatingly connected by a module space, wherein: the first device interface comprises an exhalation valve section for at least partially providing an exhalation flow of exhaled air with an exhalation pressure, the exhaled air arriving from the tube interface and flowing through the module space; the exhalation valve section includes a pressure-limiting element comprising a control section and a control element, wherein a control fluid with a control pressure is admitted to the control element; the control section is functionally connected to the control element and the exhalation pressure of the exhaled air is admitted to the control section; the pressure-limiting element is positioned, depending on the control pressure of the control fluid in the control element and depending on the exhalation pressure of the exhaled air, at least into a flow position, in which the pressure-limiting element releases the exhalation flow through the exhalation valve section, and into a blocking position, in which the pressure-limiting element blocks the exhalation flow through the exhalation valve section; and the inhalation end has a second device interface for fluid-tight connection to a second counter-device interface of an inhalation port of the ventilator of the ventilation system for providing breathing air; and a ventilator comprising: an exhalation port for removing exhaled air from the patient, wherein the exhalation port has a counter-device interface for a fluid-tight connection to the first device interface of the ventilation tube device; and an inhalation port for providing breathing air for the patient, wherein the inhalation port comprises a second counter-device interface for a fluid-tight connection to the second device interface of the ventilation tube device for providing breathing air;

receiving a triggering of a start of severing;

determining a control pressure for a control fluid, wherein an expiratory limit pressure is set in the valve module by the control pressure;

filling the control element of the valve module of the ventilation tube device with a control fluid, the control fluid having the determined control pressure; and severing the fluid-communicating connection by separating the device interface and the counter-device interface.

18. A process in accordance with claim 17, wherein the triggering is received by an input element of the ventilator.

19. A process in accordance with claim 17, wherein data comprising ventilation parameters of the ventilation of the patient and/or ventilation target variables indicating the ventilation process, are transmitted from a counter-data interface of the ventilator to a data element of the valve module in a wired and/or wireless manner.

20. A process in accordance with claim 17, wherein an expiratory limit pressure of the ventilation of the patient is determined in the step of determining the control pressure for the control fluid and the control pressure of the control fluid is determined from the expiratory limit pressure determined.

21. A process in accordance with claim 17, wherein removal of exhaled air of the patient through the exhalation port of the ventilator is stopped after the step of filling the control element of the valve module of the ventilation tube device with the control fluid.

22. A process for establishing a fluid-communicating connection between a device interface of a ventilation tube device and a counter-device interface of an exhalation port of a ventilator of a ventilation system comprising a ventilation tube device comprising: a hollow ventilation tube element with a patient end for providing breathing air to the patient and for removing exhaled air of the patient, with an inhalation end and an exhalation end, wherein the exhalation end has a counter-tube interface; and a valve module arranged at the counter-tube interface for removing exhaled air, the valve module comprising: a tube interface for fluid-tight connection to the counter-tube interface and a first device interface for fluid-tight connection to a first counter-device interface of an exhalation port of a ventilator of the ventilation system, wherein the tube interface and the first device interface are fluid-communicatingly connected by a module space, wherein: the first device interface comprises an exhalation valve section for at least partially providing an exhalation flow of exhaled air with an exhalation pressure, the exhaled air arriving from the tube interface and flowing through the module space; the exhalation valve section includes a pressure-limiting element comprising a control section and a control element, wherein a control fluid with a control pressure is admitted to the control element; the control section is functionally connected to the control element and the exhalation pressure of the exhaled air is admitted to the control section; the pressure-limiting element is positioned, depending on the control pressure of the control fluid in the control element and depending on the exhalation pressure of the exhaled air, at least into a flow position, in which the pressure-limiting element releases the exhalation flow through the exhalation valve section, and into a blocking position, in which the pressure-limiting element blocks the exhalation flow through the exhalation valve section; and the inhalation end has a second device interface for fluid-tight connection to a second counter-device interface of an inhalation port of the ventilator of the ventilation system for providing breathing air; and a ventilator comprising: an exhalation port for removing exhaled air from the patient, wherein the exhalation port has a counter-device interface for a fluid-tight connection to the first device interface of the ventilation tube device; and an inhalation port for providing breathing air for the patient, wherein the inhalation port comprises a second counter-device interface for a fluid-tight connection to the second device interface of the ventilation tube device for providing breathing air, the process comprising the steps of:

arranging the first device interface at the first counter-device interface;

determining the control pressure of the control fluid in the control element of the valve module of the ventilation tube device;

determining an expiratory limit pressure on the basis of the determined control pressure; and establishing fluid-communicating connections and starting a removal of exhaled air of the patient through the exhalation port of the ventilator with the use of the determined expiratory limit pressure.

23. A process in accordance with claim 22, wherein data comprising ventilation parameters of the ventilation of the patient, and/or ventilation target variables indicating the ventilation process are transmitted in a wired and/or wireless manner before the step of establishing fluid-communicating connections, from a data element of the valve module via a data interface of the valve module to a counter-data interface of the ventilator.

* * * * *